United States Patent [19]

Huth

[11] Patent Number: 5,389,383
[45] Date of Patent: Feb. 14, 1995

[54] METHOD FOR TREATING HYPOXIA-ASSOCIATED OCULAR COMPLICATIONS

[75] Inventor: Stanley W. Huth, Newport Beach, Calif.

[73] Assignee: Allergan, Inc., Irvine, Calif.

[21] Appl. No.: 79,025

[22] Filed: Jun. 18, 1993

[51] Int. Cl.$^6$ .............................. A61K 33/24
[52] U.S. Cl. ........................... 424/650; 514/912
[58] Field of Search ............... 424/650; 514/644, 912

[56] References Cited

U.S. PATENT DOCUMENTS 5,102,670  4/1992  Abraham et al. ............... 424/650

OTHER PUBLICATIONS

Rohde, Michael D. and Huff, Joseph W., Contact lens-induced edema in vitro-amelioration by lactate dehydrogenase inhibitors, vol. 5 No. 10, 1986, *Current Eye Research*, pp. 751–758.

Clark, M. E., Hinke, J. A. M. and Todd, M. E., Studies on Water in Barnacle Muscle Fibres II. Role of Ions and Organic Solutes in Swelling of Chemically-Skinned Fibres, *J. Exp. Biol.* (1981) 90, 43–63.

Nahas, Gabriel G., The Pharmacology of Tris (Hydroxymethyl) Aminomethane (Tham), Pharmacol. Rev., 14 (1962), pp. 447–472.

Geroski, et al., *Invest. Opthal. Vis. Sci.*, vol. 34, No. 4, 1404, 1993.

Conners, et al., *Invest. Opthal. Vis. Sci.*, vol. 33, No. 4, 780, 1992.

Nahas, Gabriel G., M.D., *Clin. Pharmacol. and Ther.*, (1963) 4, 784–802.

Primary Examiner—Zohreh Fay

[57] ABSTRACT

A method of preventing or treating hypoxia-associated ocular complications in a host in need of such prevention or treatment which comprises administering to the eye of the host a prophylactically or therapeutically effective amount of at least two agents selected from the group consisting of a heme oxygenase inducer, a membrane-permeable anti-acidosis buffer, and an osmo-protectant, as well as an aqueous ophthalmic composition useful therefor.

29 Claims, No Drawings

METHOD FOR TREATING HYPOXIA-ASSOCIATED OCULAR COMPLICATIONS

FIELD OF THE INVENTION

This invention generally relates to a method for the treatment of eye disorders. More specifically, it relates to a method and composition for preventing or treating hypoxia-associated ocular complications which employs at least two agents selected from the group consisting of a heme oxygenase inducer, a membrane-permeable anti-acidosis buffer, and an osmoprotectant agent.

BACKGROUND OF THE INVENTION

The majority of people wearing non-gas permeable hard (PMMA; polymethylmethacrylate) lenses, and a significant percentage of soft contact lens wearers experience mild to moderate corneal edema during lens wear. In "extended wear" lens users, the incidence and severity of corneal edema is greater, particularly during sleep. Other corneal complications resulting from the extended lens wear are corneal inflammation, ulcerative keratitis, infection, neovascularization, epithelial microcysts and endothelial polymegathism.

Contact lens wear causes corneal epithelial hypoxia, which results in stimulation of anaerobic glycolysis and increased production and accumulation of osmotically active lactate in the stroma. The lactate diffuses to the stroma, where it creates an osmotic imbalance leading to increased corneal hydration (swelling). The lens wear also produces an increase in $CO_2$ tension brought on by limited $CO_2$ lens transmissibility. This increase in $CO_2$ at the tear-film/lens interface, combined with accumulation of stromal lactate, contributes to a reduction in corneal pH (corneal acidosis). When the eye lids are closed, the $CO_2$ tension will increase further and the epithelial oxygen availability is reduced. These effects lead to a sustained decrease in epithelial pH while a lens is being worn and the acidification will be at its greatest when the eyes are closed. This acidification could easily lead to many corneal changes, which are responsible in part for the above-indicated corneal complications.

One solution to preventing the hypoxia would be the use of contact lens material of higher oxygen permeability (e.g., a siloxane or silicon copolymer). Unfortunately, even lenses of the highest oxygen permeabilities are known to cause significant corneal edema.

Osmotic therapy using hypertonic NaCl is being practiced, but it also affects the normal cornea. Lactate dehydrogenase (LDH) inhibitors, sodium oxalate and sodium oxamate, have been reported to inhibit the progress of experimental edema by reducing the accumulation of stromal lactate without having any effect on corneal thickness in nonedematous cornea in vitro (M. D. Rohde et al., Current Eye Research, 1986, 5, 751–758). See also M. E. Clark, J. A. M. Hinke and M. E. Todd, *J. Exp. Biol.* (1981), 90, 43–63, which is incorporated in its entirety by reference.

U.S. Pat. No. 5,102,670 to Abraham, incorporated herein by reference, discloses a method for treating or preventing ocular swelling and corneal-conjunctival inflammation. The method involves administration to the eye of an amount of a heme oxygenase inducing agent such as $SnCl_2$. See also Nahas, G. G., *Pharmacol. Rev.*, 14 (1962), 447, which is incorporated herein in its entirety by reference. An increase of heme oxygenase leads to a decrease in 12(R)-hydroxy-eicosatetraenoic acid [12(R)-HETE] and 12-hydroxy-5,8,14-eicosatrienoic acid [12(R)-DIHETE] in the arachidonic acid cascade. 12(R)-HETE is known to inhibit corneal endothelial ATPase (adenosine triphosphatase) which is an enzyme responsible for maintaining proper corneal water content and thus thickness. 12(R)-DIHETE is a chemical mediator responsible for vasodilation of conjunctival blood vessels and inflammation. Therefore, an increased level of heme oxygenase eventually leads to diminished corneal swelling and inflammation in the conjunctiva and cornea.

However, Geroski et al. *Invest. Ophthal. Vis. Sci.*, Vol. 34, no. 4, 1404, 1993, have recently shown that 12(R)-Hete can inhibit corneal endothelial ATPase by at most 29%. This fact, together with the known osmotic effects of high corneal stromal lactate to increase corneal swelling through a purely physical-chemical mechanism, and the observations of Conners et al., *Invest. Ophthal. Vis. Sci.*, Vol 33, No. 4, 780, 1992, that heme oxygenase induction reduced contact lens induced corneal swelling by only 26%, indicates that while some progress is being made to prevent hypoxia-associated corneal complications, there is a definite need for an improved method or ophthalmic composition to prevent or treat hypoxia complictions. With the advent of extended wear contact lenses, it becomes increasingly important to avoid such problems.

SUMMARY OF THE INVENTION

Surprisingly, it has been discovered that a combination of at least two agents selected from the group consisting of a heme oxygenase inducer, a membrane-permeable anti-acidosis buffer, and an osmoprotectant agent are very effective not only for treating hypoxia-associated ocular complications, but also for preventing the same in a host in need of such treatment or prevention.

In one aspect, the present invention provides a method of preventing or treating hypoxia-associated ocular complications in a host in need of such prevention or treatment which comprises administering to the eye of the host a prophylactically or therapeutically effective amount of at least two agents selected from the group consisting of a heme oxygenase inducer, a membrane-permeable anti-acidosis buffer, and an osmoprotectant.

In another aspect, the present invention provides an ophthalmic composition for preventing or treating hypoxia-associated ocular complications in a host in need of such prevention or treatment which comprises a prophylactically or therapeutically effective amount of at least two agents selected from the group consisting of a heme oxygenase inducer, a membrane-permeable anti-acidosis buffer and an osmoprotectant, together with a physiologically acceptable carrier.

In general, the present invention involves administration to the eye of a subject an ophthalmic composition including (a) up to about 2.5% by weight of a heme oxygenase inducer; (b) up to about 0.5M of a membrane-permeable anti-acidosis buffer; (c) up to about 0.6M of an osmoprotectant; (d) up to about 2.0% by weight per volume of a tonicity adjusting agent; and (e) water, wherein the composition has a pH range of about 6.0 to about 9.0 and wherein at least two components selected from (a), (b) and (c) are present in the composition.

DETAILED DESCRIPTION OF THE INVENTION

The ophthalmic compositions of the present invention are physiologically acceptable in that they are safe and tolerable in the eye and have no significant ocular side effects.

While the composition is open to the inclusion of various other ingredients that will not detract from its efficacy, stability or physiological acceptance, preferred examples of the ingredients are provided below for purposes of illustrative clarity.

As used herein, the term "prophylactically effective amount" means that the amount of the active ingredients contained in the composition is of sufficient quantity to prevent hypoxia-associated complications by administration of the composition prior to, or simultaneously with, exposure of a host to a condition where such complications are anticipated. For example, when contact lens wear is expected to continue for an extended period of time, prior or simultaneous administration of the composition would be required.

As used herein, the term "therapeutically effective amount" means that the amount of the active ingredients is of sufficient quantity to abrogate or ameliorate hypoxia-associated complications by administration of the composition before, simultaneously or after a host has developed clinical signs and symptoms resulting from such complications.

Both amounts can vary greatly according to the effectiveness of each active ingredient, the age, weight, and response of the individual host as well as the nature and severity of the host's clinical signs and symptoms. Accordingly, there is no upper or lower critical limitation upon the amount of the active ingredient. The required quantity to be employed in the present invention can readily be determined by those skilled in the art.

As used herein, the term "hypoxia-associated ocular complications" refers to any adverse conditions in which the eye or parts thereof, such as the cornea and conjunctiva, develop arising from prolonged contact lens wear which causes a state of hypoxia.

The ophthalmic composition of the present invention principally employs at least two agents selected from the group consisting of a heme oxygenase inducer, a membrane-permeable anti-acidosis buffer, and an osmoprotectant, together with a physiologically acceptable carrier.

The heme oxygenase inducer includes any compound known to induce heme oxygenase in vivo. Representative compounds are heme derivatives, heavy metal ions, and Vitamin $B_{12}$. Suitable heavy metal ions are an ion of a metal selected from the group consisting of Cr, Mn, Fe, Ni, Cu, Zn, Au, Hg, Pb, Cd, Sn, Pt and Sb. The most preferred metal ion is $Sn^{+2}$ or $Sn^{+4}$. Stannous chloride, being physiologically acceptable, is a particularly preferred compound. Suitable heme derivatives are various synthetic hemes wherein Fe is replaced by other metals such as Sn, Cr, Co, Zn, or Mn, and analogous compounds wherein the porphyrin ring structure is modified as protoporphyrins or mesoporphyrins. Typical synthetic hemes are cobalt protoporphyrin (CoPP), cobalt mesoporphyrin (CoMP), and heme arginate.

An effective concentration range for the heme oxygenase inducer in the composition of the invention is generally from about 0.0005 to about 1.0 w/v %, more preferably 0.001 to 0.2 w/v % and even more preferably about 0.02 w/v %.

The membrane-permeable anti-acidosis buffer may be included in the composition to correct corneal acidosis. In general, the requirements of the buffer are: (1) it must permeate through the corneal epithelium into the interior of epithelial cells and thus must be able to buffer the intracellular pH of epithelial cells; (2) it must pass through the epithelium into the stroma and buffer acellular stromal tissue and (3) it must be acceptable from a safety and toxicology point of view. Thus, suitable buffers should be soluble in tears, physiologically acceptable, act as a proton acceptor in vivo and be capable of permeating through the corneal epithelial cell membranes into the intracellular medium of the epithelial cells and must also be capable of permeating through the entire corneal epithelium into the corneal stroma. The most preferred buffer is a weak base, tris(hydroxymethyl)aminomethane (TRIS) or alternatively di(hydroxymethyl) aminomethane. TRIS has been used for the treatment of acute respiratory acidosis or metabolic acidosis which develops during cardiac operations because of its low toxicity and excellent buffering ability (G. G. Nahas, *Clin. Pharmacol. and Ther.*, (1963), 4, 784–802). Other organic amines can be used. Sodium bicarbonate and hydroxide ion can also be used. An effective concentration range for the membrane-permeable anti-acidosis buffer is generally from about 0.05M to about 0.50M, more preferably 0.10M to 0.30M.

The osmoprotectant may be included in the composition to regulate intracellular and/or extracellular osmotic pressure. The osmoprotectant can thus correct the uneven and/or elevated hydration across the cornea (cornea swelling) caused by the lactate accumulation. Suitable osmoprotectants which can be used include trimethylamine N-oxide (TMAO), betaine, sarcosine, glycine and glycine derivatives (e.g., dimethylglycine), N,N-bis(2-hydroxyethyl) glycine, amino acids (e.g., L-alanine, D-alanine and $\beta$-alanine), taurine, glycerol, I-aminocyclopropane-I-carboxylic acid, octopine and trehalose. The particularly preferred osmoprotectant is TMAO. An effective concentration range for the osmoprotectant is generally from about 0.05M to about 0.6M, more preferably 0.10M to 0.40M.

It should be noted that osmoprotectants such as glycine or its active derivatives (e.g., sarcosine, dimethylglycine and betaine) or other suitable osmoprotectants (e.g., TMAO) can be used alone or with other excipients to treat hypoxia in the form of a tablet to be ingested or other suitable delivery vehicle. The glycine then is believed to build up in the wearer's system to afford protection from the hypoxia induced complications of contact lens wear.

The heme oxygenase inducer, the membrane-permeable anti-acidosis buffer, and the osmoprotectant of the present invention can be co-administered to the eye of a host in a single combined formulation such as eye drops and eye washes. Alternatively, they can be administered concurrently as separate dosage forms. Still further, one agent can be administered before or after administration of the other agent(s) provided that the time interval between the two (or three) is not too lengthy, i.e., not more than a few hours. It is, however, for convenience to the patient and the prescribing ophthalmologist to use the agents as a single composition or formulation. Preferably and conveniently, the combined agents are administered in combination with a physiologically acceptable carrier. The most preferred carrier is sterile purified water. Tonicity adjusting agents are normally required in an ophthalmic composition. The function of the tonicity adjusting agents is to make the composition physiologically acceptable to ocular tissues and to increase the comfort level upon administration. Suitable such agents include alkali metal halides, phosphates, hydrogen phosphates, and borates. Preferred are sodium chloride, potassium chloride, sodium phosphate monobasic and sodium phosphate dibasic. Typically, sodium chloride can be present in the composition in an amount of from about 0% to about 2.0% by weight per volume of the total, more preferably in amount of about 0% to about 0.4%. Thus, the composition of the present invention can be prepared by dissolving the active components directly in the aforementioned vehicle, or the composition of the present invention can be added to known ophthalmic solutions.

In another mode of administration, the active agents of the invention may be administered to the eye in the form of a time release system, such as a contact lens, bandage lens or wafer. Such wafer systems are well known to the ophthalmological art, and are used when a uniform, controlled delivery of the active agents is desired. These systems may be made of biocompatible and biodegradable materials which degrade in the eye upon contact with a body fluid (tears) or an enzyme, and are subject to the same pharmacologically acceptable requirements as are indicated for the aforementioned solutions. In yet another method of administration an osmoprotectant selected from the group consisting of glycine, L-alanine, D-alanine, $\beta$-alanine, l-aminocyclopropane-l-carboxylic acid, sarcosine, dimethylglycine, betaine, taurine, TMAO (trimethylamineoxide) and mixtures thereof can be combined with a hemeoxygenase inducer such as stannous chloride and Vitamin B-12, and the resulting composition ingested. Of the osmoprotectants for use in this mode of administration, glycine is preferred.

Additional ingredients may be added to the composition, as long as they are physiologically acceptable and not deleterious to the eye or ocular tissue. Further, they should not adversely affect the efficacy of the above-noted active components as well as should not deteriorate the stability of the composition. Additional ingredients are, for example, stabilizers, preservatives, disinfecting agents, buffering agents (when the anti-acidosis buffer is not present in the composition) and the like. Such ingredients are known to those skilled in the ophthalmological art. For example, suitable preservatives and disinfecting agents include polyhexamethylene biguanide, polyquad (Onamer M), and polyoxyalkylene diamine biguanides. Generally, preservatives and disinfecting agents may be used at a concentration level of about 0.5 to 100 ppm. Suitable buffers include sodium or potassium citrate, citric acid, boric acid, sodium borate, sodium bicarbonate, various mixed phosphate buffers including combinations of $Na_2HPO_4$, $NaH_2PO_4$, $Na_3PO_4$, $K_2HPO_4$, $KH_2PO_4$ and $KHCO_3$. Generally, buffers may be used in an amount from about 0.05% to 2.5% by weight per volume of the total and preferably 0.1% to 2.0%. Thus, the pH of the present composition is buffered to prevent irritation to the eye by adding the buffer to the composition for pH adjustment. This buffer requirement is separate and distinct from the buffering requirements to impart anti-acidosis characteristics to the composition. In other words, the compositions can be buffered with ordinary buffers to impart pH-stability and ocular-acceptability in addition to the requirement to provide a unique membrane-permeable anti-acidosis buffer.

When contemplating the use of the active components of the invention in a contact lens wetting solution, many additional ingredients can be included in the solution to wet or rewet contact lenses in the eye. These ingredients are antimicrobial or antifungal agents, surfactants, viscosity-building agents such as lecithin or hydroxymethylcellulose, detergent cleaners, and the like. Representative compounds for each ingredient and their use levels are ascertainable to those skilled in the ophthalmic art. For example, U.S. Pat. No. 4,529,535 fully teaches the state of art, the disclosure of which is herein incorporated by reference.

The active components of the invention can be provided in solid form such as tablets or powders. Effervescing agents are typically employed when the composition is provided in solid form. Examples of suitable effervescing agents include tartaric or citric acid used in combination with a suitable alkali metal salt such as sodium carbonate.

The effectiveness of the compositions of the present invention to prevent or ameliorate hypoxia-associated ocular complications can be determined by their ability to pass two or more of the following standard biological and/or pharmacological tests, viz, (1) measuring their ability to induce heme oxygenase to a level which adequately controls inflammation and swelling; (2) measuring their ability to reduce or eliminate corneal swelling (e.g. osmotically-induced swelling); and (3) measuring their ability to shifting corneal epithelial and stromal pH to a physiologically acceptable value.

While the present invention has been described with respect to preferred embodiments thereof, it will be understood that various changes and modifications will be apparent to those skilled in the art and that it is intended that the invention encompass such changes and modification as falling within the scope of the appended claims. The following non-limiting examples are provided to further illustrate the present invention.

EXAMPLE 1

The following ingredients were combined and mixed uniformly together to produce an ophthalmic composition having a pH of 8.3:

| Ingredients | Amount (% by weight) |
| --- | --- |
| Stannous chloride | 0.02 |
| TRIS | 1.49 |
| TRIS Hydrochloride salt | 0.79 |
| Sodium Chloride | 0.34 |
| Polyhexamethylene biguanide (PHMB) | 1 ppm |
| Disodium EDTA | 0.01 |
| Sterile distilled water | qs ad 100 ml |

EXAMPLE 2

The following ingredients were combined and mixed uniformly together to produce an ophthalmic composition having a pH of 7.4:

| Ingredients | Amount (% by weight per volume) |
| --- | --- |
| Stannous chloride | 0.02 |
| TMAO | 3.3 |
| Sodium phosphate (dibasic) | 0.12 |
| Sodium phosphate monobasic | 0.02 |
| PHMB | 1 ppm |
| Disodium EDTA | 0.01 |

-continued

| Ingredients | Amount (% by weight per volume) |
|---|---|
| Sterile distilled water | qs ad 100 ml |

EXAMPLE 3

The following ingredients were combined and mixed uniformly together to produce an ophthalmic composition having a pH of 8.3 and osmolality of 364 mosm.:

| Ingredients | Amount (% by weight per volume) |
|---|---|
| TRIS | 1.49 |
| TRIS Hydrochloride salt | 0.79 |
| TMAO | 1.53 |
| PHMB | 1 ppm |
| Sterile distilled water | qs ad 100 ml |

I claim:

1. A method of preventing or treating hypoxia-associated ocular complications in a host in need of such prevention or treatment which comprises administering to the eye of the host a prophylactically or therapeutically effective amount of at least two agents selected from the group consisting of a heme oxygenase inducer, a membrane-permeable anti-acidosis buffer, and an osmoprotectant.

2. The method according to claim 1, wherein the heme oxygenase inducer is stannous chloride.

3. The method according to claim 1, wherein the buffer is tris(hydroxymethyl)aminomethane.

4. The method according to claim 1, wherein the osmoprotectant is trimethylamine N-oxide.

5. The method according to claim 1, wherein the administration is in the form of a liquid.

6. The method according to claim 5, wherein the liquid is an eye wash, eye drops, saline solution, contact lens disinfecting or multi-purpose solution.

7. The method according to claim 1, wherein the administration is in the form of time release system.

8. The method according to claim 7, wherein the time release system is a contact lens, bandage lens or degradable wafer.

9. The method according to claim 1, wherein the method is principally directed to preventing the hypoxia-associated ocular complications and the administration is conducted prior to or simultaneous with wearing of a contact lens by the host.

10. The method according to claim 1, wherein the method is principally directed to treating the hypoxia-associated ocular complications and the administration is conducted simultaneous with or after wearing of a contact lens by the host.

11. The method according to claim 1, wherein the hypoxia-associated ocular complication is corneal edema.

12. The method according to claim 1, wherein the hypoxia-associated ocular complication is ocular inflammation.

13. An ophthalmic composition for preventing or treating hypoxia-associated ocular complications in a host in need of such prevention or treatment which comprises a prophylactically or therapeutically effective amount of at least two agents selected from the group consisting of a heme oxygenase inducer, a membrane-permeable anti-acidosis buffer, and an osmoprotectant, together with a physiologically acceptable carrier.

14. The composition according to claim 13, wherein the heme oxygenase inducer is stannous chloride.

15. The composition according to claim 13, wherein the buffer is tris(hydroxymethyl)aminomethane.

16. The composition according to claim 13, wherein the osmoprotectant is trimethylamine N-oxide.

17. The composition according to claim 13, wherein the heme oxygenase inducer and the membrane-permeable anti-acidosis buffer are selected.

18. The composition according to claim 13, wherein the heme oxygenase inducer and the osmoprotectant are selected.

19. The composition according to claim 13, wherein the membrane-permeable anti-acidosis buffer and the osmoprotectant were selected.

20. An ophthalmic composition comprising:
   (a) up to about 2.5 w/v % of a heme oxygenase inducer;
   (b) up to about 0.5M of a membrane-permeable anti-acidosis buffer;
   (c) up to about 0.6M of an osmoprotectant;
   (d) up to about 2.0% by weight per volume of a tonicity adjusting agent,
wherein the composition has a pH range of from about 6.0 to about 9.0, provided that at least two components selected from (a), (b), and (c) are present in the composition.

21. The composition according to claim 20, wherein the heme oxygenase inducer is stannous chloride.

22. The composition according to claim 20, wherein the buffer is tris(hydroxymethyl)aminomethane.

23. The composition according to claim 20, wherein the osmoprotectant is trimethylamine N-oxide.

24. The composition according to claim 20, wherein the tonicity adjusting agent is sodium chloride.

25. The composition according to claim 20, wherein the tonicity agent is present in an amount of from 0 to about 1.0% by weight per volume of the total.

26. The composition according to claim 20, further comprising a preservative.

27. The composition according to claim 26, wherein the preservative is polyhexamethylene biguanide.

28. A method of treating hypoxia induced complications of contact lens wear comprising forming a composition including an osmoprotectant and formulating the composition in an ingestible vehicle.

29. The method of claim 28 wherein the composition includes glycine or its active derivatives.

* * * * *